United States Patent [19]

Fekete et al.

[11] Patent Number: 4,774,090

[45] Date of Patent: Sep. 27, 1988

[54] STABILIZED INSECTICIDAL COMPOSITION AND PROCESS FOR THE PREPARATION THEREOF

[75] Inventors: Pal Fekete; Karoly Magyar; Anna Mayer nee Almasi; Jozsef Kelemen; Katalin Toth, all of Budapest, Hungary

[73] Assignee: Egyt Gyogyszervegyeszeti GYAR, Budapest, Hungary

[21] Appl. No.: 562,575

[22] PCT Filed: Apr. 6, 1983

[86] PCT No.: PCT/HU83/00014

§ 371 Date: Dec. 2, 1983

§ 102(e) Date: Dec. 2, 1983

[87] PCT Pub. No.: WO83/03521

PCT Pub. Date: Oct. 27, 1983

[30] Foreign Application Priority Data

Apr. 6, 1982 [HU] Hungary .............................. 1042/82

[51] Int. Cl.[4] ..................... A01N 25/28; A01N 25/34; A61K 9/50
[52] U.S. Cl. ................................... 424/408; 424/418; 424/494
[58] Field of Search .................. 424/35, 408, 418, 494

[56] References Cited

U.S. PATENT DOCUMENTS 3,912,815 10/1975 Henrick et al. ............. 260/410.9 N

OTHER PUBLICATIONS

Harris et al. "Horn Flies and Stable Flies" Free Choice Feeding of Methopreve Mineral Blocks to Cattle for Control J. Eco. Ent 67:3843810.
CA. 99(4):28007a "Cellulose Acetate Phthalate Microencapsulation" Felcete et al.

Primary Examiner—Allen J. Robinson
Attorney, Agent, or Firm—Herbert Dubno; Jonathan Myers

[57] ABSTRACT

The invention relates to a microencapsulated insecticidal composition containing isopropyl (2E,4E)-3,7,11-trimethyl-11-methoxy-2,4-dodecaidenoate which comprises 45-95% by weight of isopropyl (2E,4E)-3,7,11-trimethyl-11-methoxy-2,4-dodecadenoate as active ingredient, 1-15% by weight of butyl hydroxy toluene and 5-40% by weight of activated charcoal, in the form of powdery microcapsules having a grain size of 1-300 μm and coated with a hydroxypropyl methyl cellulose phthalate or cellulose acetate phthalate polymer.

The advantage of the microencapsulated insecticidal composition according to the present invention resides in the increased stability.

8 Claims, No Drawings

STABILIZED INSECTICIDAL COMPOSITION AND PROCESS FOR THE PREPARATION THEREOF

TECHNICAL FIELD

The invention relates to a stabilized insecticidal composition comprising isopropyl (2E,4E)-3,7,11-trimethyl-11-methoxy-2,4-dodecadienoate, said composition being used in admixture with cattle feed. The composition of the invention is suitable for inhibiting the propagation of flies in the cattle excrement.

BACKGROUND ART

It is known that isopropyl (2E,4E)-3,7,11-trimethyl-11-methoxy-2,4-dodecadienoate (referred to furtheron as methoprene) exhibits useful insecticidal effects (U.S. Pat. No. 3,904,662).

According to U.S. Pat. No. 3,912,815 polymeric capsules comprising methoprene can be used for the extermination of undeveloped insects living on or under the surface of soil.

According to J. Eco. Entomol. 67, 69–70 (1974) methoprene as a juvenile hormone estergase inhibiting substance when applied onto the larvae of different Diptera species is capable of inhibiting the energence of the imagos from the nymphs. The effective concentration of methoprene might vary depending on the larvae of the different species. According to in vitro tests 10 ppm of methoprene added to the dung completely inhibits the energence of imago from the nymphes formed from the larvae of the *Musca autumnalis* species. In the case of *Musca domestica* a concentration of 100 ppm resulted in an inhibition of 90%. A similar effect was observed on the larvae of *Stomoxys calcitrans* too, while methoprene proved to be the most effective against the larvae of *Haematobia irritans*. Due to its high activity and very low toxicity methopren can enter the excrement by feeding the methoprene to the animals. On oral administration the following activity was found against the most important fly species.

*Haematobia irritans*[1]: 0.002 mg/kg body weight/day, 100% effect;
*Stomoxys calcitrans*[2]: 0.4 mg/kg body weight/day, 100% effect;
*Musca autumnalis*[2]: 0.5 mg/kg body weight/day, 99% effect;
*Musca domestica*[3]: 10.0 mg/kg body weight/day, 80% effect (1) R. L. Harris, E. D. Frazer and R. L. Younger: J. Eco. Entomol. 66, 1099–1102 (1973),
(2) R. W. Miller, L. G. Pickens; J. Eco. Entomol. 68, 810–812 (1975),
(3) R. W. Miller, E. C. Uebel: J. Eco. Entomol. 67, 69–70 (1974).

According to hitherto applied practical methods cattle ingest methoprene either dissolved in the drinking water or admixed with the salt or proteine fodder. The drawback of consumption of the drinking water is that uniform concentration can only be ensured by using expensive specific equipment. The safest ingestion in the form of a solid nutriment consists of the addition of methoprene to mineral salt additives since said additives are more widespreadly used in cattle husbandry than other feed additives. At the same time said use encounters difficulties because as a result of chemical lability of methoprene the active ingredient content of said compositions decreases very rapidly, particularly when used for cattle grazing on pasture land, where the weather conditions—first of all sunshine—accelerate the chemical decomposition to a large extent. Thus, according to J. Eco. 67, 384–386 (1974) the active ingredient content of salt blocks comprising 0.9% of methoprene and stored in a store-house for 9 weeks decreases by 13–30%. According to J. Eco. Entomol. 71, 274–278 (1978) in a salt mixture stored under field conditions the average decrease of the active ingredient content within 10 days amounts to 26%.

DISCLOSURE OF INVENTION

The object of the invention is to provide a stabilized methoprene composition which overcomes the above disadvantages of the known formulations.

It has been found that the decomposition of methoprene can be slowed down by means of antioxidants and light-protecting agents. As antioxidant butyl hydroxy toluene can be used. The known light protecting agents are, however, unsuitable for use in the present invention for food hygienic reasons.

It has been surprisingly found that by using activated charcoal, which is harmless from a hygienical point of view, excellent results can be obtained.

The present invention is based on the recognition that by dissolving 1–15% by weight of butyl hydroxy toluene and suspending 5–40% by weight of activated charcoal in technical grade methoprene and transforming the suspension thus obtained into a powder having a grain size of 1–300 μm by a suitable microencapsulating method, the triple protection—namely anti-oxidant effect, light-protecting effect and barrier effect of the wall of the microcapsules—ensures suitable stability of methoprene.

According to the present invention there is provided a microencapsulated insecticidal composition containing isopropyl (2E,4E)-3,7,11-trimethyl-11-methoxy-2,4-dodecadienoate which comprises 45–95% by weight of isopropyl (2E,4E)-3,7,11-trimethyl-11-methoxy-2,4-dodecadienoate as active ingredient, 1–15% by weight of butyl hydroxy toluene and 5–40% by weight of activated charcoal, in the form of powdery microcapsules having a grain size of 1–300 μm and coated with a hydroxypropyl methyl cellulose phthalate or cellulose acetate phthalate polymer.

According to a further feature of the present invention there is provided a process for the preparation of a microencapsulated insecticidal composition containing isopropyl (2E,4E)-3,7,11-trimethyl-11-methoxy-2,4-dodecadienoate which comprises admixing 40–95% by weight of isopropyl (2E,4E)-3,7,11-trimethyl-11-methoxy-2,4-dodecadienoate as active ingredient with 1–15% by weight of butyl hydroxy toluene and 5–40% by weight of activated charcoal, adding the suspension thus obtained to a solution of hydroxypropyl methyl cellulose phthalate or cellulose acetate phthalate and preparing from the mixture thus obtained powdery microcapsules having a grain size of 1–300 μm by microcapsulating methods known per se.

For the purposes of the present invention any suitable known microencapsulating method can be used. If hydroxypropyl methyl cellulose phthalate is used, the process described and claimed in pending Hungarian patent application Ser. No. EE-2625 can be particularly preferably used. According to this process microcapsules are prepared by dispersing the substrate to be coated in an aqueous solution of a hydroxypropyl methyl cellulose phthalate polymer in the presence of sodium hydroxide or a salt of a strong base formed with a weak acid, decreasing the pH value of the system below 4.5 and increasing the temperature above 30° C. If cellulose acetate phthalate is used, the process disclosed and claimed in pending Hungarian patent application Ser. No. 2648/80 can be particularly advantageously applied. According to this process microcapsules are prepared by flocculating onto the substrate to be coated heat-treated cellulose acetate phthalate in a strong electrolyte medium and thereafter diluting and acidifying the system.

The hydroxypropyl methylcellulose phthalate has the following formula:

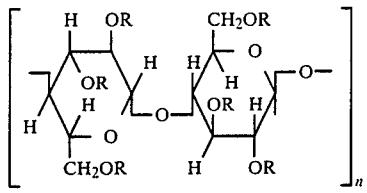

wherein R is a methyl, hydroxypropyl, phthalyl, or hydrogen substituent, and the ratio of the substituents is 18 to 25% methyl, 6 to 12% hydroxypropyl, 20 to 35% phthalyl, and 28 to 56% hydrogen.

The cellulose acetate phthalate is the partial ester of cellulose formed with acetic acid and phthalic acid and having an acetyl content of 17 to 24% and a phthalyl content of 30 to 40%.

According to a preferred embodiment of the present invention there is provided a licking salt for cattle comprising isopropyl (2E,4E)-3,7,11-trimethyl-11-methoxy-2,4-dodecadienoate microencapsulated as disclosed above in an amount of 0.01–1% by weight.

Said licking salt for cattle can be prepared by admixing microencapsulated isopropyl (2E,4E)-3,7,11-trimethyl-11-methoxy-2,4-dodecadienoate insecticidal composition disclosed above with sodium chloride—in an amount of 0.01–1% by weight, related to the weight of the sodium chloride—and pressing blocks from the mixture thus obtained.

The stabilized microencapsulated insecticidal methoprene composition according to the present invention can be fed up by cattle or other ruminants and the methoprene content thereof enters the excrement of the animals and there inhibits the propagation of the fly species in the dung.

The powdery product obtained by microencapsulation facilitates on the one hand the admixture of methoprene being liquid at room temperature with various premixes, while on the other hand the wall of the microcapsule separates the methoprene molecules from the metal ions which are present in the salt premix and which exhibit a catalytic effect; thus in addition to the antioxidant effect of butyl hydroxy toluene and the light protecting effect of activated charcoal, this contributes to an increased stability of the composition. The powdery microcapsule thus obtained decomposes on storage neither per se nor when admixed with various premixes or ready-for-use fodders. Moreover, the microcapsules according to the present invention show suitable stability under field conditions when placed on the grazing pasture land and it is suitable for the significant decrease of the fly population in cattle kept on the pasture field.

INDUSTRIAL APPLICABILITY

The microencapsulated product of the present invention is added to various premixes in an amount which corresponds to the daily fodder consumption required to efficient inhibition of the propagation of flies such as the Haematobia, Musca and Stomosys species.

According to the safest method of uniform addition of methoprene the microencapsulated composition of the present invention is admixed with the salt additive serving as mineral salt supply or is incorporated into the licking salt blocks. The daily licking salt consumption of grazing cattle amounts to about 20–40 g. accordingly by using salt with a methoprene content of about 0.02–0.03% the methoprene dose of 0.002 mg/kg body weight/day required to exterminate the Haematobia species can be safefly provided.

MODES OF CARRYING OUT THE INVENTION

Further details of the present invention—including the composition, said preparation and comparative stability data—are shown in the following Examples without limiting the invention to the Examples which serve merely as illustration.

EXAMPLE 1

Preparation of compositions with and without an activated charcoal content and comparison of the stability thereof (a) In 25.0 g of methoprene 0.25 g of butyl hydroxy toluene are dissolved whereupon 2.5 g of activated charcoal are suspended in the solution. The suspension thus obtained is dispersed in a solution of 12.5 g of cellulose acetate phthalate and 250 g of 0.6% aqueous sodium hydroxide solution until a drop size of 1–10 μm is reached. The system is diluted by adding 375 ml of water, and 125 ml of a 20% aqueous sodium sulfate solution is added at room temperature under constant stirring. The system is diluted with a further 125 ml of water, cooled to 0°–5° C. whereupon 200 ml of a 1.5% citric acid solution and thereafter 90 ml of a 10% citric acid solution are added under constant stirring until the pH is equal to 3.5–4. The mixture is heated to 60° C., stirred at this temperature for an hour, cooled again, filtered, and dried. Thus, a black powder consisting of fine grains and having an active ingredient content of about 55% is obtained.

(b) Methoprene microcapsules containing 5% of butyl hydroxy toluene and 10% of activated charcoal are prepared in an analogous manner to the process disclosed in paragraph (a).

(c) The process disclosed in paragraph (a) is carried out except that no activated charcoal is added. Thus a yellowish fine powder having an active ingredient content of about 65% and containing no activated charcoal is obtained.

The microcapsules thus obtained are admixed with fodder grade sodium chloride to yield a salt mixture containing 0.02% of methoprene. The salt mixture is spread out in a layer having a thickness of 1 cm and subjected to UV illumination with a 750 W mercury vapor lamp from a height of 50 cm.

Illumination is carried out for 4 hours. The methoprene content of the salt mixture after illumination is determined and the percental decrease of methoprene content is calculated. The results are summarized in the following Table I.

TABLE I

| Test | Amount of butyl hydroxy toluene | Amount of activated charcoal | methoprene content after illumination |
|---|---|---|---|
| (a) | 1% | 10% | 80% |
| (b) | 5% | 10% | 100% |
| (c) | 1% | 0% | 14.28% |

It appears from the above Table that in the absence of activated charcoal the methoprene content decreases to one-seventh of the original value, while by using the composition of the present invention the reduction of the methoprene content amounts but to 0-20%.

EXAMPLE 2

Stability test under storage and under field conditions of microencapsulated methoprene composition containing active charcoal Microcapsules containing 5% of butyl hydroxy toluene and 10% of activated charcoal, related to the methoprene content, are prepared according to Example 1, paragraph (b). The microcapsules thus obtained are incorporated into a fodder salt to yield a salt mixture having a methoprene content of about 0.02%. From the mixture thus obtained blocks (diameter 16.5 cm; height: about 15 cm) are pressed with the aid of a suitable equipment. Samples of the salt blocks are stored under normal conditions (temperature 20°-30° C., relative humidity 40-70%) while other salt block samples are stored under field conditions in July and August on cattle pasture land for 6 weeks.

The methoprene content of the salt blocks stored under different conditions is determined and the results are summarized in the following Table II.

TABLE II

| Sample | Methoprene content |
|---|---|
| Original sample before storage | 0.023% |
| After storing in a store-house for 8 weeks | 0.023% |
| After storing for 6 weeks under field conditions in the upper 0-1 cm layer of the salt block | 0.015% |
| in the 1-3 cm layer under the upper layer | 0.020% |
| in the inner layer under the 3 cm layer | 0.021% |
| average methoprene content | 0.0205% |

The above data show that the active ingredient content of salt blocks containing stabilized methopren microcapsules does not decrease during 8 weeks' storage. Under field conditions the average weekly decrease of the active ingredient content amounts to about 2% a week, which is significantly lower than the weekly value of about 20% disclosed in prior art.

Further stability test is carried out by using salt blocks which contain 0.030% of stabilized methoprene microcapsules of the present invention. The results are set forth in Table III.

TABLE III

| Sample | Methoprene content |
|---|---|
| Original sample before storage After storing in a store-house for 8 months | 0.030% |
| in the upper 0-1 cm layer of the salt block | 0.020% |
| in the 1-3 cm layer under the upper layer | 0.030% |

TABLE III-continued

| Sample | Methoprene content |
|---|---|
| in the inner layer under the 3 cm layer | 0.030% |

Thus, during an 8 months' storage in a store-house a decrease of the active ingredient content of about 27% is observed only in the upper 1 cm layer, while in the inside of the salt block the methoprene content does not change at all.

EXAMPLE 3

Biological activity of microencapsulated methoprene composition containing activated charcoal The salt blocks prepared according to Example 2 are placed into open storers and used for the salt supply of cattle grazing on a pasture field. The animals are given free excess to the salt blocks. The herd consists of 170 animals, 1 salt block is used for 10 animals and the salt supply is made up approximately every 10 days, depending on the rate of ingestion. As control group a cattle herd grazing about 2 kilometers away from the test herd is used.

The composition of the fly population which infects the grazing cattle is determined before treatment (at the beginning of July) and the number of the flies on the side of the treated and untreated animals is counted during treatment. It has been found that in the period between the 10th day following the treatment and the end of the treatment (six weeks) the number of the flies found on the treated animals is by about 80% less than that on the untreated animals. This corresponds to the original ratio of the most dangerous and harmful Haematobia species in the fly population.

According to an another evaluation method 3-4 days' old samples are taken from the excrement of treated and untreated animals. The insects emerging from the eggs laid in the excrement are bred in the laboratory and the ratio of the various species is determined. It has been found that in the treated group the number of flies belonging to the Haematobia species is by 97% less than in the untreated group.

What we claim is:

1. A microencapsulated insecticidal composition comprising isopropyl (2E,4E)-3,7,11-trimethyl-11-methoxy-2,4-dodecadienoate which comprises 45-95% by weight of isopropyl (2E,4E)-3,7,11-trimethyl-11-methoxy-2,4-dodecadienoate as active ingredient, 1-15% by weight of butyl hydroxy toluene and 5-40% by weight of activated charcoal, in the form of powdery microcapsules having a grain size of 1-300 μm and coated with a hydroxypropyl methyl cellulose phthalate or cellulose acetate phthalate polymer.

2. The composition according to claim 1 as a licking salt for cattle comprising 0.01-1% by weight of a microencapsulated isopropyl (2E,4E)-3,7,11-trimethyl-11-methoxy-2,4-dodecadienoate insecticidal composition according to claim 1.

3. A method of treating cattle which comprises administering to the cattle salt blocks including an effective amount of a microencapsulated insecticidal composition comprising isopropyl (2E,4E)-3,7,11-trimethyl-11-methoxy-2,4-dodecadienoate which comprises 45-95% by weight of isopropyl (2E,4E)-3,7,11-trimethyl-11-methoxy-2,4-dodecadienoate as active ingredient, 1-15% by weight of butyl hydroxy toluene and 5-40% by weight of activated charcoal, in the form of powdery microcapsules having a grain size of 1-300 μm and coated with a hydroxypropyl methyl cellulose phthalate or cellulose acetate phthalate polymer.

4. A microencapsulated insecticidal composition comprising isopropyl (2E,4E)-3,7,11-trimethyl-11-methoxy-2,4-dodecadienoate which comprises 100 parts by weight of the isopropyl (2E,4E)-3,7,11-trimethyl-11-methoxy-2,4-dodacadienoate as active ingredient, 1 to 5 parts by weight of butyl hydroxy toluene, and 10 parts by weight of activated charcoal, in the form of powdery microcapsules having a grain size of 1 to 300 μm and coated with a hydroxypropyl methylcellulose phthalate or cellulose acetate phthalate polymer, wherein the hydroxypropyl methylcellulose phthalate has the formula:

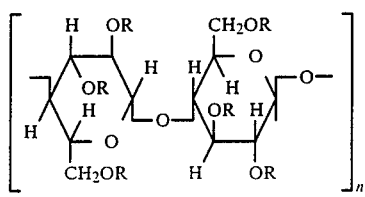

wherein R is a methyl, hydroxypropyl, phthalyl or hydrogen substituent and the ratio of the substituents is 18 to 25% methyl, 6 to 12% hydroxypropyl, 20 to 35% phthalyl, and 28 to 56% hydrogen; and wherein the cellulose acetate phthalate is the partial ester of cellulose formed with acetic acid and phthalic acid with an acetyl content of 17 to 24% and a phthalyl content of 30 to 40%.

5. The microencapsulated insecticidal composition defined in claim 4 which comprises 1 part by weight of butyl hydroxy toluene.

6. The microencapsulated insecticidal composition defined in claim 4 which comprises 5 parts by weight of butyl hydroxy toluene.

7. The microencapsulated insecticidal composition defined in claim 4 as a licking salt for cattle comprising 0.01 to 1% by weight of a microencapsulated isopropyl (2E,4E),-3,7,-11-trimethyl-11-methoxy-2,4-dodecadienoate insecticidal composition according to claim 6.

8. A method of treating cattle which comprises administering to the cattle salt blocks including an effective amount of the microencapsulated insecticidal composition comprising isopropyl (2E,4E)-3,7,11-trimethyl-11-methoxy-2,4-dodecadienoate as defined in claim 4.

* * * * *